United States Patent
Schätzl et al.

(10) Patent No.: US 8,157,743 B2
(45) Date of Patent: Apr. 17, 2012

(54) DEVICE AND METHOD FOR EVALUATING A SIGNAL INDICATIVE OF THE RESPIRATION OF A PERSON

(75) Inventors: Stefan Schätzl, Weilheim (DE); Jörg Meier, Munich (DE); Aleksandra Dana-Mika, Munich (DE); Thomas Betzl, Kirchseon (DE); Oliver Lange, Germering (DE)

(73) Assignee: MAP Medizin-Technologie GmbH, Martinsried (DE)

( * ) Notice: Subject to any disclaimer, the term of this patent is extended or adjusted under 35 U.S.C. 154(b) by 1157 days.

(21) Appl. No.: 11/665,766

(22) PCT Filed: Oct. 21, 2005

(86) PCT No.: PCT/EP2005/011358
§ 371 (c)(1), (2), (4) Date: Dec. 4, 2007

(87) PCT Pub. No.: WO2006/045559
PCT Pub. Date: May 4, 2006

(65) Prior Publication Data
US 2008/0119755 A1    May 22, 2008

(30) Foreign Application Priority Data
Oct. 21, 2004  (DE) .......................... 10 2004 051 373

(51) Int. Cl.
*A61B 5/08* (2006.01)
(52) U.S. Cl. ........................................ 600/538; 600/529
(58) Field of Classification Search .......... 600/529–543
See application file for complete search history.

(56) References Cited

U.S. PATENT DOCUMENTS

| | | | |
|---|---|---|---|
| 5,363,857 A | 11/1994 | Howard et al. | |
| 5,520,192 A | 5/1996 | Kitney et al. | |
| 6,290,654 B1 * | 9/2001 | Karakasoglu ................. | 600/529 |
| 7,722,546 B2 * | 5/2010 | Madaus et al. ................ | 600/538 |

(Continued)

FOREIGN PATENT DOCUMENTS

EP  0 256 435  2/1988

(Continued)

OTHER PUBLICATIONS

Guler et al. "Two-stage classification of respiratory sound patterns." 2005. Computers in Biology and Medicine, 35:67-83.*

(Continued)

*Primary Examiner* — Miranda Le
*Assistant Examiner* — Meredith Weare
(74) *Attorney, Agent, or Firm* — Nixon & Vanderhye PC

(57) ABSTRACT

A device and a method for evaluating a signal that can indicate the respiration of a person, particularly suitable for examining a patient with respect to the occurrence of sleep-related breathing disturbances. In one example, a device for evaluating a signal indicative of the temporal course of the respiration of a patient, in particular a respiratory flow signal, includes an electronic evaluation program or circuitry which is configured in such a manner that it evaluates the signal by continuously generating intermediate evaluation results for short signal periods and for longer signal periods being parallel thereto, and performs an identification of respiratory patterns in the time signal or in specific time periods on the basis of the position of the intermediate evaluation results of the short signal periods relative to the intermediate evaluation results of the longer signal periods.

23 Claims, 2 Drawing Sheets

U.S. PATENT DOCUMENTS

| | | | |
|---|---|---|---|
| 7,827,988 B2 * | 11/2010 | Matthews et al. | 128/204.21 |
| 2004/0230105 A1 * | 11/2004 | Geva et al. | 600/301 |
| 2005/0043645 A1 * | 2/2005 | Ono et al. | 600/529 |
| 2008/0177195 A1 * | 7/2008 | Armitstead | 600/529 |

FOREIGN PATENT DOCUMENTS

| | | | |
|---|---|---|---|
| JP | 2001346880 A | * | 12/2001 |

OTHER PUBLICATIONS

International Preliminary Report on Patentability (IPRP) issued in PCT/EP2005/011358 on May 3, 2007.

International Search Report for PCT/EP2005/011358 mailed Mar. 21, 2006.

* cited by examiner

Strip method for detecting respiratory patterns strip segment sequence n1 strip segment sequence n2 strip segment sequence n3 strip segment sequence n4 strip segment sequence n-n2 strip segment sequence n-n1 strip segment sequence n

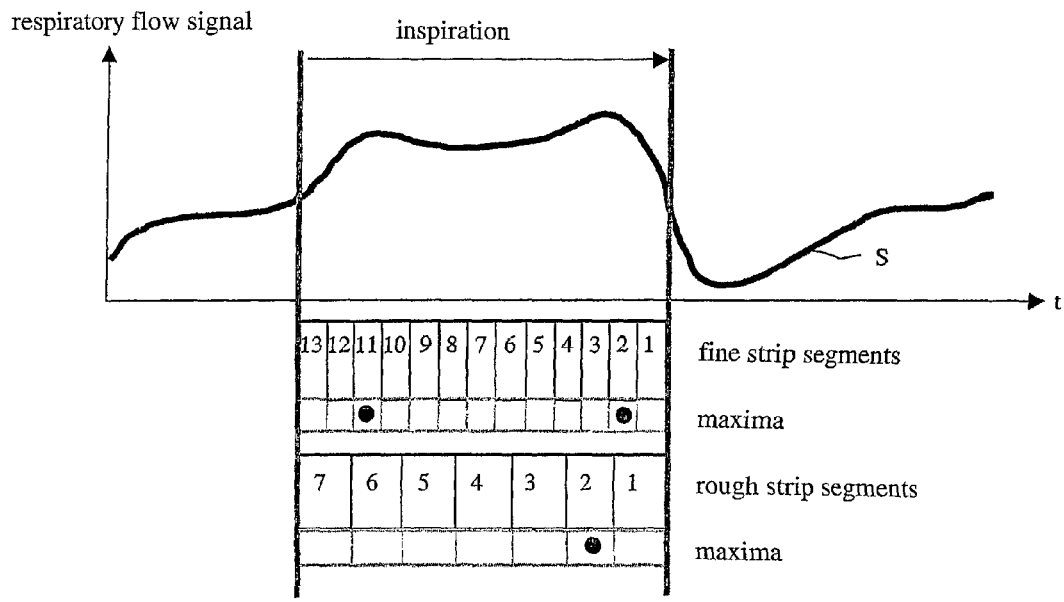

Fig. 2

Evaluation

| | number of maxima in the fine strip segment sequence | number of maxima in the rough strip segment sequence | positions of maxima in the fine strip segment sequence | positions of maxima in the rough strip segment sequence | further features |
|---|---|---|---|---|---|
| | 2 | 1 | 11.2 | 2 | --- |
| criteria for flow-limited breath fulfilled | yes | yes | yes | yes | --- |

Evaluation:
The form of the breath fulfills the criteria of flow limitations

Fig. 3

DEVICE AND METHOD FOR EVALUATING A SIGNAL INDICATIVE OF THE RESPIRATION OF A PERSON

This application is the US national phase of international application PCT/EP2005/011358 filed Oct. 21, 2005 which designated the U.S. and claims priority to DE 10 2004 051 373.2 filed Oct. 21, 2004 the entire contents of each of which are hereby incorporated by reference.

The present invention relates to a device and a method for evaluating a signal that is indicative of the respiration of a person. A signal evaluation of this kind is particularly suitable for examining a patient with respect to the occurrence of sleep-related breathing disturbances. A signal evaluation of this kind can furthermore also be used for adjusting and controlling the respiratory gas pressure of respiratory gas supply devices. Corresponding diagnosis and respiratory gas supply devices are used, in particular, for the diagnosis of sleep-related respiratory disturbances and for the treatment of such sleep-related respiratory disturbances by means of positive pressure respiration.

It is the object of the present invention to provide a device and a method by means of which phases and properties which are relevant to the control and diagnosis, in particular respiratory patterns in the temporal course of the respiration of a patient, can be detected with a sufficiently high reliability.

In view of the device, this object is achieved in accordance with the present invention by means of a device for evaluating a signal that is indicative of the temporal course of the respiration of a patient, in particular a respiratory flow signal, by means of an electronic evaluation means (which may include a processor) which is configured in such a manner that it evaluates the signal by continuously generating intermediate evaluation results for short signal periods and for longer signal periods being parallel thereto and performs an identification of respiratory patterns in the time signal or in specific time periods on the basis of the position of the intermediate evaluation results of the short signal periods relative to the intermediate evaluation results of the longer signal periods.

It is thus possible in an advantageous manner to reliably examine a signal that was generated by a differential pressure measuring means and is indicative of a respiratory gas flow with respect to the occurrence of specific respiratory patterns contained in the respiratory gas flow. The respiratory patterns which were detected in this manner can form the basis for a diagnosis by a doctor. It is also possible to influence the respiratory gas pressure to be applied to a patient on the basis of the thus performed respiratory pattern detection by a correspondingly self-adjusting respirator either simultaneously or with a suitable temporal delay.

The duration of the short signal periods is preferably dimensioned such that one inspiration phase is divided into at least ten, preferably 13 signal periods. The duration of the longer signal periods is preferably dimensioned such that one inspiration phase is divided into a number of longer signal periods which corresponds approximately to half the number of periods in which the inspiration phase is divided into short signal periods. The number of longer signal periods is therefore dimensioned such that one inspiration phase is divided into seven signal periods.

The signal is preferably divided again into parallel longer signal periods, wherein intermediate evaluation results, which are included in the identification process, are again generated for said longer signal periods.

The intermediate evaluation results preferably consist of an indication whether or not a signal period contains a local extreme value relative to a previous and a following time period of the signal with respect to the respiratory gas flow.

The respiratory pattern is preferably detected on the basis of the mutual positions of signal periods representing extreme values. It is possible to define mutual relative positions of the intermediate evaluation results of the different signal periods in the form of a matrix and for specific respiratory patterns. In particular also OR operation or disjunction can be provided in said fulfillment matrix.

It is possible to dampen the generation of the intermediate evaluation results in a defined manner, e.g. by making sure that an extreme value attribution does not take place before a defined value difference between the previous and the following breath has been detected. This defined value difference can be defined so as to be static or also variable.

In accordance with a particularly preferable embodiment of the invention, the respiratory phase is detected on the basis of the position of the evaluation results relative to the short and longer time periods. To this end, respective criteria are preferably provided in a criteria matrix intended for the respiratory phase change. It is possible to use criteria which differ from the criteria of the expiration phase for the inspiration phase.

The invention is also directed to a method for evaluating a signal that is indicative of the temporal course of the respiration of a patient, in particular a respiratory flow signal, thereby using an electronic evaluation means which is configured for carrying out said method and in which intermediate evaluation results are continuously generated for short signal periods and longer signal periods parallel thereto and respiratory patterns in the temporal signal are identified on the basis of the position of the intermediate evaluation results of the short signal periods relative to the intermediate evaluation results of the longer signal periods.

Modifications and preferred embodiments of both device and method can be taken from the dependent claims, wherein the features according to any one of the dependent method claims preferably also relate to the claimed device and furthermore, wherein the features according to any one of the dependent device claims preferably also relate to the claimed method.

Further details and features of the invention can be taken from the following description in combination with the drawings in which FIG. 1 is a diagram illustrating the attribution of individual time frames with respect to their temporal lengths for generating intermediate evaluation results;

FIG. 2 is a representation directed to an inspiration phase for explaining the detection of local short-time maxima and local long-time maxima;

FIG. 3 is a table exemplarily explaining the evaluation of the strip segments according to FIG. 2.

Figure 1:
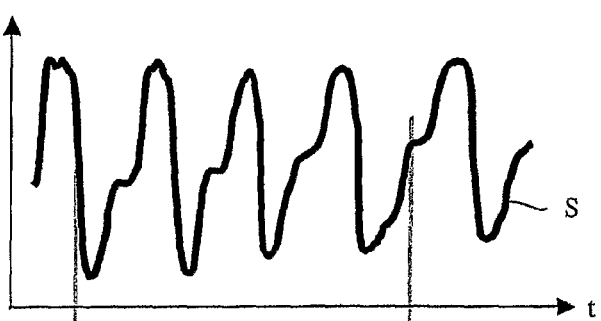
Figure 1:
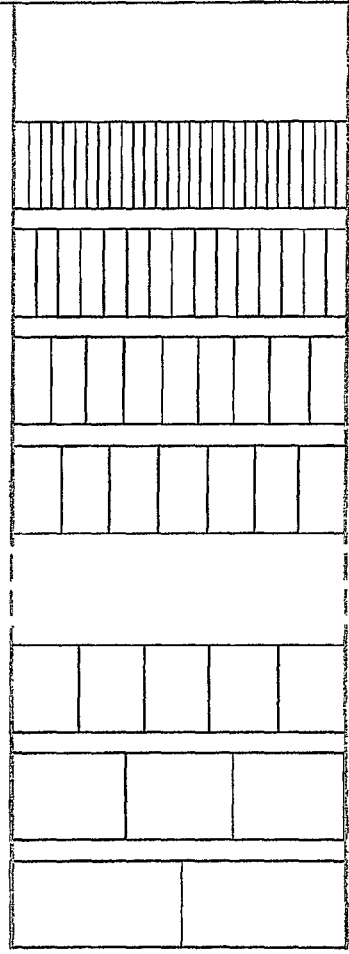

It is evident from FIG. 1 that a respiratory flow signal S, which is indicative of the temporal course of the respiratory gas flow, is examined in view of the respiratory patterns and breath periods contained therein. In the depicted example, the signal S describes five subsequent breaths.

Intermediate evaluation results which are dimensioned differently as regards their temporal length, i.e. differently "rough" time periods are generated for these breaths. These intermediate evaluation results are attributed to the respective strip segments within a strip segment sequence n1, n2, n3, n4, etc. On the basis of the mutual temporal positions of the intermediate evaluation results obtained for defined time frames, specific respiratory patterns can be detected on the basis of functional criteria or logic operation criteria. It is possible to define functional criteria which allow a classification of the respective breath, e.g., as a flow-limited or normal breath. It is also possible to define evaluation criteria on the basis of which it is possible to detect respiratory patterns whose distinctness becomes only evident in connection with a plurality of breaths.

In this diagram, the strip segment sequence n1 is shown only exemplarily with a time frame segmentation which is already relatively rough as compared to the length of the shown breath. In the concrete application, the temporal length of the strip segments is preferably adjusted such that a typical breath is divided into at least ten short signal periods. The temporal length of the individual time frames within a strip segment sequence can be determined statically. However, it is also possible to determine the temporal length of the time frames in such a manner that an entire breath or in particular also the inspiration phase thereof is always divided into a predetermined number of strip segments, i.e. to adapt it breath-specifically.

The strip segments can be numbered or specified in accordance with their time positions. An intermediate evaluation result, which is generated from the respiratory flow signal on the basis of a predetermined intermediate evaluation criterion, can be attributed to the respective strip segment. Intermediate evaluation results are in particular results which show whether the signal S has an extreme value relative to the signal values in neighboring time frames within the time frame attributed to the respective strip segment. On the basis of the mutual positions of the extreme values determined in specific strip segments, a respiratory pattern detection or in particular also a respiratory phase detection can be performed by means of a functional or optional matrix.

The present examination of the signal S, which is indicative of the respiratory gas flow, by means of the shown evaluation in time frames which have different temporal lengths and overlap each other allows in particular the detection of obstructive respiratory disturbances, mainly flow limitations, expiratory mouth breathing, hypopnea, flow reductions, RERA and apnea. This method moreover allows the detection of central respiratory disturbances, mainly Cheyne-Stokes respiration, central and mixed apnea as well as periodic respiration. Moreover, also general respiratory disturbances or even system disturbances, e.g. leakage as well as periodic leakage can be detected. For these breath properties, it is possible to determine suitable fulfillment criteria for the mutual positions of intermediate evaluation results.

On the basis of the described strip method, any respiratory flow signal can be examined for specific respiratory patterns. The examination ranges can be used for the inspiration and expiration phases per breath period as well as for intervals of breaths or a specific number of data points to be examined.

The evaluation for each strip (frame within the sequence) can take place in such a manner that said strip receives pieces of information which can be analyzed with other ranges within a group and/or among each other with other groups. The information contained in one strip can be, e.g.: minimum, maximum, first derivative, second derivative, average value, standard deviation, time, time intervals, temporal relationships between inspiration, expiration and overall length of breath, correlation.

The thus obtained intermediate evaluation results can be evaluated by means of matrix systems. Criteria which have to be fulfilled when a respiratory pattern to be detected is present are defined in the respective matrix systems.

FIG. 2 shows in a temporally extended mariner the course of the signal S, which is indicative of the respiratory gas flow, in particular in an inspiration phase. This inspiration phase is exemplarily divided into 13 short strip segments and seven rougher strip segments. Local maxima can be seen in each of the short strip segments 2 and 11. The rough strip segment 2 shows an absolute maximum of the value of the signal S in the inspiration phase. By functionally assessing the evaluation results in the fine strip segments in relation to the evaluation results in the rough strip segments, it is evident from the table according to FIG. 3 that the shown breath, which is depicted in segments, has to be classified as a flow-limited breath.

The above concept of examining and evaluating a signal that is indicative of the temporal course of the respiration can be used for a more or less automated detection of respiratory patterns. Moreover, on the basis of a respiratory pattern detection of this kind it is also possible to determine desired pressure levels for the supply of a breathable gas.

The above concept for detecting respiratory patterns can be used as follows, in particular in an auto-CPAP device.

For carrying out a CPAP therapy, a so-called auto-CPAP device is coupled to the patient to be treated via a flexible tube and a respiratory mask. The auto-CPAP device first supplies the patient with ambient air having a pressure level being adjusted to the falling-asleep phase and lying above the ambient pressure level. Via a flow sensor, which is integrated into the auto-CPAP, the respiratory gas flow is continuously detected. The measuring signals generated in this connection are supplied to an electronic signal processing means. Said electronic signal processing means is configured so as to successively generate intermediate evaluation results for time frames which are different with respect to their temporal lengths but extend in parallel. Said intermediate evaluation results are functionally assessed. By means of said functional assessment, it is possible to detect occurring respiratory patterns on the basis of the fulfillment of predetermined functional patterns in the recorded signal.

When specific respiratory patterns occur, the pressure can be increased or, if necessary, also decreased. For example, when flow-limited breaths occur, it is possible to increase the respiratory gas pressure gradually, e.g. by about 2 mbar, until there are no longer any limitations in the respiratory pattern. As soon as no properties that can be regarded as an indication of flow limitations have been detected for a predetermined time period, the respiratory gas pressure can be decreased again gradually. It is thus possible to carry out the positive pressure respiration on the basis of the lowest pressure level appropriate for the treatment.

The invention claimed is:

1. A device for evaluating a respiratory flow signal that is indicative of the temporal course of the respiration of a patient, the device comprising:
   a processor configured to
   (a) evaluate the signal by continuously generating intermediate evaluation results for first signal temporal periods and for second signal temporal periods, wherein said second signal temporal periods are parallel to said first signal temporal periods and longer in duration than said first signal temporal periods, and
   (b) perform an identification of respiratory patterns in the respiratory flow signal based on a position of first intermediate evaluation results of the first signal temporal periods relative to second intermediate evaluation results of the second signal temporal periods, wherein said respiratory patterns are indicative of a disturbance or a phase change.

2. The device according to claim 1, wherein the duration of the first signal temporal periods is dimensioned such that one inspiration phase is divided into ten signal segments.

3. The device according to claim 1, wherein the duration of the first signal temporal periods is dimensioned such that one inspiration phase is divided into at least 13 signal segments.

4. The device according to claim 1, wherein the duration of the second signal temporal periods is dimensioned such that one inspiration phase is divided into a number of longer signal periods which corresponds approximately to half the number of periods in which the inspiration phase is divided into first signal temporal periods.

5. The device according to claim 1, wherein the number of second signal temporal periods is dimensioned such that one inspiration phase is divided into at least seven signal periods.

6. The device according to claim 1, wherein the respiratory flow signal is divided again into third signal temporal periods and third intermediate evaluation results, which are included in the identification process, are again generated for said third signal temporal periods, wherein said third signal temporal periods are parallel to said first signal temporal periods and said second signal temporal periods, and different in duration from the first and second signal temporal periods.

7. The device according to claim 1, wherein the intermediate evaluation results comprise an indication as to whether or not a signal period contains a local extreme value relative to a previous and a following time period of the signal.

8. The device according to claim 1, wherein the respiratory pattern is detected based on mutual positions of signal segments representing an extreme value.

9. The device according to claim 1, wherein an extreme value attribution does not take place before a defined value difference between the previous and the following breath has been detected.

10. The device according to claim 1, wherein a respiratory phase is detected based on the position of the evaluation results relative to the first and second signal temporal periods.

11. The device according to claim 1, wherein criteria which differ from the criteria of the expiration phase are used for the inspiration phase.

12. The device according to claim 1, wherein both of the first and second signal temporal periods correspond to regular adjacent time intervals that extend throughout the same temporal course of the respiration of the patient.

13. A method for evaluating a respiratory flow signal that is indicative of the temporal course of the respiration of a patient, the method comprising:
(a) evaluating, via a processor, said respiratory flow signal by continuously generating intermediate evaluation results for first signal temporal periods and second signal temporal periods wherein said second signal temporal periods are parallel to said first signal temporal periods and longer in duration than said first signal temporal periods, and
(b) identifying, via the processor, respiratory patterns in the respiratory flow signal based on a position of first intermediate evaluation results of the first signal temporal periods relative to second intermediate evaluation results of the second signal temporal periods, wherein said respiratory patterns are indicative of a disturbance or phase change.

14. The method according to claim 13, further comprising detecting local minimum values of the respiratory flow signal as intermediate evaluation results.

15. The method according to claim 13, further comprising detecting local maximum values of the respiratory flow signal as intermediate evaluation results.

16. The method according to claim 13, further comprising detecting the values of the first derivative of the respiratory flow signal as intermediate evaluation results.

17. The method according to claim 13, further comprising detecting the values of the second derivative of the respiratory flow signal as intermediate evaluation results.

18. The method according to claim 13, further comprising detecting the values of the standard deviation of the respiratory flow signal as intermediate evaluation results.

19. The method according to claim 13, further comprising detecting the average values of the respiratory flow signal in the corresponding time period as the intermediate evaluation results.

20. The method according to claim 13, further comprising detecting, as intermediate evaluation results, time intervals and/or temporal relationships between inspiration, expiration,. and overall length of breath 21. The method according to claim 13, further comprising detecting the backward correlations of the values of the first derivative of the respiratory flow signal as intermediate evaluation results.

22. The method according to claim 13, further comprising detecting respiratory patterns by examining the intermediate evaluation results via matrix systems, wherein criteria that have to be fulfilled when a respiratory pattern to be detected is present are defined in the respective matrix systems.

23. The method according to claim 13, wherein both the first and second signal temporal periods correspond to regular adjacent time intervals that extend throughout the same temporal course of the respiration of the patient.

* * * * *